United States Patent [19]

Daiberl

[11] 4,332,556

[45] Jun. 1, 1982

[54] ALIGNING ASSEMBLY FOR USE IN DENTISTRY

[76] Inventor: Karl Daiberl, Untersbergstrasse 4, 8000 München 90, DE, Fed. Rep. of Germany

[21] Appl. No.: 890,190

[22] Filed: Mar. 27, 1978

[30] Foreign Application Priority Data

Mar. 28, 1977 [DE] Fed. Rep. of Germany ... 7709769[U]

[51] Int. Cl.³ .............................................. A61C 19/04
[52] U.S. Cl. ........................................ 433/69; 433/68
[58] Field of Search ...................... 32/9, 21, 19, 20, 17, 32/18, 1; D24/10, 11, 16; 433/71, 72, 68, 7, 69

[56] References Cited

U.S. PATENT DOCUMENTS

| 475,928 | 5/1892 | Carroll | 433/7 |
|---|---|---|---|
| 1,397,082 | 11/1921 | Cox | 32/9 |
| 2,301,358 | 11/1942 | Ballard | 433/69 |
| 2,760,267 | 8/1956 | O'Donnell | 32/19 |
| 3,068,570 | 12/1962 | Thompson et al. | 433/69 |
| 3,314,152 | 4/1967 | Frush | 32/19 |
| 3,564,717 | 2/1971 | Ennor | 32/19 |
| 3,724,099 | 4/1973 | Stuart | 32/19 |

OTHER PUBLICATIONS

"A Scientific Method of Establishing Normal Vertical Dimension", J. L. Armstrong, Jour. A.D.A., vol. 30, Nov. 1, 1943.

*Primary Examiner*—Gene Mancene
*Assistant Examiner*—Michael J. Foycik
*Attorney, Agent, or Firm*—Michael J. Striker

[57] ABSTRACT

An aligning assembly for use in dentistry, particularly in prosthodontics and/or orthodontics includes two plates each of which is to be positioned in the oral cavity of a patient at the upper jaw and to the lower jaw, respectively. One of the plates has a projection which, subsequent to an initial positioning of the plates in the oral cavity, and while the patient moves the lower jaw relative to the upper jaw, provides a centering mark on the other plate. At least the other plate is of an inexpensive, easily deformable material so that, upon removal of the jaw plates from the oral cavity, a recess can be provided in the place of the centering mark on the other plate. When the two plates are repositioned in the oral cavity to be connected to each other to form the assembly, the projection is partially received in the recess and fixes the plates with respect to each other against misalignment while they are being connected. The connection between the plates may be established by providing at least one body of an adhesive which bonds the plates to one another prior to the removal of the connected assembly from the oral cavity of the patient.

2 Claims, 7 Drawing Figures

ALIGNING ASSEMBLY FOR USE IN DENTISTRY

BACKGROUND OF THE INVENTION

The present invention relates to an aligning assembly for use in prosthodontics, occlusion diagnosis and/or occlusion therapy in general, and more particularly to such an assembly which includes rigid upper jaw and lower jaw components which are connected to one another, after being properly positioned with respect to one another, to form the assembly for further use in dental work.

Aligning assemblies of this type are already in use and usually they include an upper jaw plate and a lower jaw plate one of which is provided with a bore in which there is received an externally threaded pin which is introducable into the other jaw plate.

One conventional aligning assembly of this kind has, in common with other similar aligning assemblies, both of the plates made of a metallic material. In addition thereto, there is provided a gauging support of a synthetic plastic material which is adjustably connected with the lower jaw plate by means of a pin-and-slot connection, the gauging support having a recess into which the point of the pin affixed to the upper jaw plate is elastically introducible. The alignment provided in an assembly of this type by means of the pin has considerable advantages when compared to the manual taking of the bite, especially with respect to the exact adjustment of the two condyles in the corresponding hinges.

In this conventional assembly, the two biting plates are fittingly positioned on the upper jaw or on the lower jaw, respectively, whereafter the patient is asked to conduct anterior-posterior and lateral movements of his lower jaw relative to the upper jaw. During these movements, the point of the pin draws a centering mark on the corresponding surface of the lower jaw plate which has been previously provided with a coating, such as a color coating. Thereafter, the dentist so positions the synthetic plastic material gauging support on the lower jaw plate that the recess of the gauging support registers with the centering mark. Then, the gauging support is fixed in position with respect to the lower jaw plate by means of a screw which enters the slot of the gauging support. Thereafter, the biting plates are repositioned in the oral cavity of the patient. After this happens, the patient is advised to close his mouth with a slight pressure, thus introducing the tip of the pin in the recess of the gauging support. After this, the dentist introduces an impression mass between the two plates. When the impression mass has hardened, both of the biting plates can be jointly removed from the oral cavity of the patient.

While this conventional arrangement is suited for precision work, the fact remains that this type of an aligning assembly has not yet been so widely used as it would deserve, particularly in view of the fact that the use of the known aligning assembly is relatively complicated and not free from sources of errors. So, for instance, the adjustment of the gauging support and the fixation by the impression mass which, more often than not, includes plaster and similar substances, are cumbersome operations which can lead to a mistaken taking of the bite. During the fixation with the plaster, it often happens that the biting plates are shifted relative to one another while the patient, particularly a nervous patient, moves his or her cheeks or jaws, finding this operation uncomfortable. When the tip of the pin is to be introduced into the recess of the gauging support during the taking of the bite, there exists the danger that the gauging support may become displaced. Furthermore, it cannot be always exactly ascertained whether the patient has indeed hit the recess of the gauging support or whether the gauging support remained in its position during the closing of the patient's mouth. A further source of errors is to be seen in the fact that the exact adjustment of the gauging support with respect to the centering mark is often rendered very difficult by reflection in the synthetic plastic material. Moreover, the possibilities of application of the known aligning assembly are drastically limited by the fact that the conventional aligning assembly can be used only on jaws which do not have any teeth whatsoever.

SUMMARY OF THE INVENTION

Accordingly, it is a general object of the present invention to avoid the disadvantages of the prior art.

More particularly, it is an object of the present invention to develop a registering assembly of the type here under consideration which is not possessed of the disadvantages of the prior-art registering assemblies for use in dental work.

A further object of the present invention is to so construct the aligning assembly as to keep the possibilities of error to a minimum if not eliminate them altogether.

A concomitant object of the present invention is to provide a registering assembly which is simple in construction, inexpensive to manufacture, easy to use and reliable nevertheless.

Still another object of the present invention is to design a registering assembly for use in dental work which can be used regardless of the number of teeth which the patient has on respective jaws.

Furthermore, it is an object of the present invention to provide a method of making an aligning assembly of the type here under consideration which is significantly simplified in comparison with the methods of making the prior-art assemblies of this type. In pursuance of these objects and other which will become apparent hereafter, one feature of the present invention resides, in an aligning assembly for use in prosthodontics, occlusion diagnosis and/or occlusion therapy, wherein the aligning assembly includes an upper jaw plate and a lower jaw plate one of which has a bore therein and an externally threaded pin received in the bore and adapted to abut the other plate, briefly stated, in the improvement wherein the plates are of a synthetic plastic material. A prominent advantage obtained when the aligning assembly is made of synthetic plastic material is that an arresting action can be obtained, in a very simple manner, in that a recess or a through hole can be drilled into the previously aligned other plate in the place indicated by the centering mark, by resorting to the usual and readily available crown drill, the recess or through hole then arrestingly receiving the tip of the pin during the taking of the bite.

According to a further aspect of the present invention, there is provided means for connecting the components to one another in the above-mentioned given position with the projection received in the recess, which includes at least one, but preferably more than one, body of an adhesive substance which bonds the components to one another.

Advantageously, the method of making an aligning assembly for use particularly in the prosthodontic and orthodontic work, comprises the steps of positioning an upper jaw component and a lower jaw component, one of which has a projection thereon, in the oral cavity of a patient; causing the components to move toward each other until the projection abuts the other component and then along each other for the projection to provide a centering mark on the other component; removing the components from the oral cavity; forming a recess in the place of the centering mark; repositioning the components in the oral cavity; causing the components to move toward each other until the projection partially enters the recess; and connecting the components to each other to form the assembly of the components prior to the removal thereof from the oral cavity. Preferably, the connecting step includes forming at least one, but preferably more than one, body of an adhesive substance on at least one of the components prior to the above-mentioned repositioning step for the adhesive substance to bond the components to each other subsequent to the partial entry of the projection into the recess. Advantageously, two or three heaps of a quick-hardening synthetic plastic material can be provided on the lower biting plate, which bond with the upper biting plate when the patient closes his mouth subsequent to the repositioning of the biting plates in his or her oral cavity. Thus, the assembly and the method of the present invention dispenses with the fixation by the plaster and with the conventional gauging support and the necessary adjustment thereof. Thus, the patient is not inconvenienced. Unwanted and possibly unrecognized shiftings of the pin relative to the centering mark during the taking of the bite are eliminated, inasmuch as the aligning assembly according to the present invention does not require the presence of the conventional gauging support and the recess for the tip of the pin is provided directly in the opposite biting plate.

A further advantage of the novel aligning assembly is to be seen in the fact that, when the jaws of the patient include at least some teeth, the respective biting plate can be cut out around the available teeth. In addition thereto, the respective plate, when the corresponding jaws contains at least some teeth, can be connected to these available teeth by a synthetic plastic material or the like.

Advantageously, the plates have a dull luster finish or a rough finish on those surfaces thereof which face each other in the assembly. In this manner, there is obtained an unobjectionable bonding with the synthetic plastic material heaps. On the other hand, any coating, especially a color coating, which may be provided on the respective surface in order to form the centering mark therein, also adheres perfectly to the respective surface.

In this connection, it has been established that it is particularly advantageous when the bite plates have a thickness of between 0.5 and 1.5 millimeters, preferably approximately 1 millimeter. A biting plate of such a thickness, on the one hand, has the required rigidity and, on the other hand, can be rapidly and simply drilled through and possibly cut out.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENT

Figure 1:
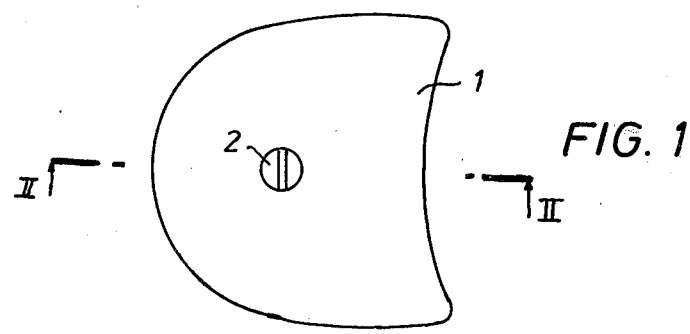
FIG. 1 is a top plan view of the upper jaw biting plate.
Figure 2:
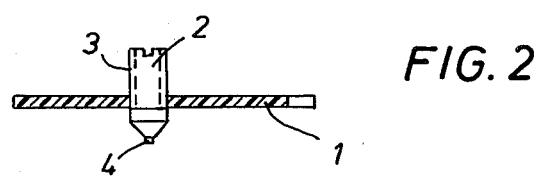
FIG. 2 is a section taken on line II—II of FIG. 1.

Referring now to the drawing in detail, and first to FIGS. 1 and 2 thereof, it may be seen that the reference numeral 1 has been used to designate an upper jaw biting plate. The bite or biting plate 1 consists of a synthetic plastic material and has a thickness of approximately 1 millimeter. A pin 2 is threadedly received in a bore of the biting plate 1. The pin 2 is provided, on a cylindrical part thereof, with an external thread 3 which renders it possible to adjust the distance between a tip 4 of the pin 2 and the lower side of the biting plate 1. The smallest possible distance can amount to approximately 1 millimeter. This distance is determined by the spacing between the end of the external thread 3 which is lowermost in FIG. 2, and the tip 4 of the pin 2. Preferably tip 4 is of ball-shaped configuration.

Figure 3:
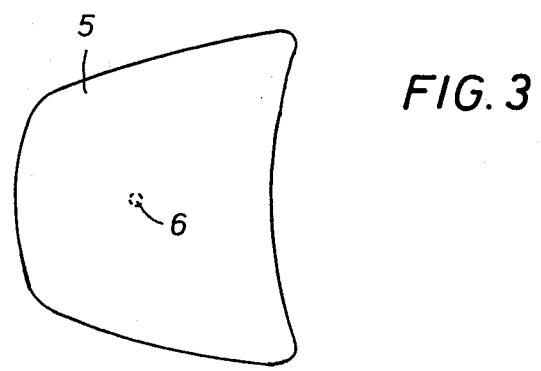
FIG. 3 is a top plan view of a lower jaw biting plate of the invention.

A lower jaw biting plate 5 is illustrated in FIG. 3 and is also made of a synthetic plastic material and has a thickness of approximately 1 millimeter. The reference numeral 6 indicates the location at which a bore is to be provided in the place of a centering mark on the biting plate 5. During the taking of the bite, the tip 4 of the pin 2 is arrestingly received in the bore 6 of the biting plate 5. The pin 2 can be made of metal or also of a synthetic plastic material. If tip 4 is ball-shaped, bore 6 has a diameter slightly smaller than that of tip 4 thereby providing for an exactly predetermined depth of penetration of tip 4 in bore 6.

Figure 6:
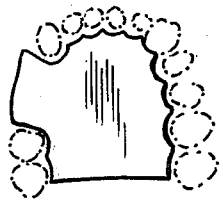
FIG. 6 is a top plan view of a hower life plate applied to a partially toothed jaw.
Figure 7:
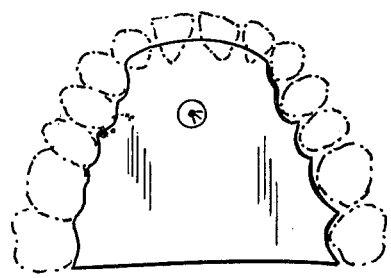
FIG. 7 is a plan view of an upper life plate applied to a fully toothed jaw.

Having so discussed the construction of the assembly of the present invention, the method of using the same for dental, especially prosthodontic or orthodontic purposes, will be briefly discussed. In this respect, it is to be mentioned that the positioning of the plates 1 and 5 on the jaws of the patient is too well known to require any discussion here. Suffice it to say that, when the patient still has some teeth in his respective jaws, the plates are cut out in the places of the still existent teeth and then positioned on the jaws (FIG. 6). Also, when none or only some of the teeth are missing, the biting plates 1 and 5 can be connected directly to the existing teeth, after having been cut out according to the contour of the teeth (FIG. 7), by a suitable synthetic plastic material or the like. This is particularly useful in orthodontics.

Figure 5:
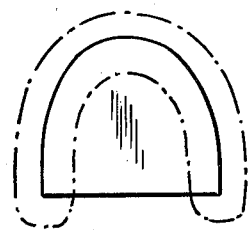
FIG. 5 is a top plan view of a lower life plate applied to a toothless jaw.

If the jaw (FIG. 5) has no teeth, a base plate of plastic material is adapted to and pressed on the jaw on which it is held by subatmospheric pressure between jaw and base plate. The biting plate then is fixed on the base plate, preferably by wax.

Figure 4:
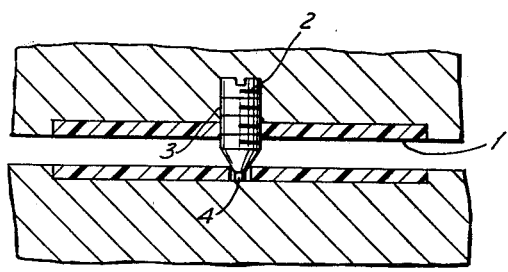
FIG. 4 is a sectional side view of aligned bite plates.

After the biting plates 1 and 4 have been initially properly positioned in the oral cavity of the patient, he or she is advised to close the mouth until the tip 4 of the pin 2 abuts the facing surface of the lower jaw biting plate 5 which is provided with the above-mentioned distinctive coating (FIG. 4). Thereafter, the patient is asked to conduct anterior-posterior and lateral movements with his or her lower jaw, during which movements the tip 4 of the pin 2 provides a centering mark on the distinctive coating. After that, at least the lower jaw biting plate 5 is removed from the oral cavity of the user and the recess or through hole 6 is drilled into the lower jaw biting plate 5 in the place of the above-mentioned centering mark. Then, two or three heaps of quick-hardening synthetic plastic material may be provided on the upper surface of the lower jaw biting plate 5, and the latter is repositioned within the oral cavity of the patient. Subsequently, as the patient again closes his or her mouth, the tip 4 of the pin 2 will enter the recess or hole 6 to be arrestingly received therein so that no shifting of the biting plates 1 and 5 relative to one another will occur during the hardening of the material of the adhesive heaps and its bonding to the upper jaw biting plate 1.

The mutually facing surfaces advantageously have a dull luster finish or a rough finish, which facilitates the adhesion of the distinctive coating to the lower jaw biting plate 5, and the bonding of the synthetic plastic material heaps to the respective biting plates 1 and 5. After the quick-hardening synthetic plastic material has hardened and thus bonded the biting plates 1 and 5 to one another, the thus-obtained assembly is removed from the oral cavity of the patient and subsequently used in prosthodontic or orthodontic work.

It will be understood that each of the elements described above, or two or more together, may also find a useful application in other types of constructions differing from the types described above.

While the invention has been illustrated and described as embodied in a registering assembly for use in prosthodontics and orthodontics, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of determining correct mandibular position, particularly in prosthodontic and orthodontic work, comprising the steps of providing two prefabricated flat, rigid plates of a standard shape exceeding the inner contour of the parient's gums, and made of plastic material, one of said plates having a projection thereon; marking said plates according to the inner contour of existent teeth; adjusting the edges of the plates by cutting off the portions thereof exceeding the marked contours; positioning the adjusted plates in the oral cavity to rest on the upper gum and the lower gum, respectively, whereby the projection abuts the other plate; having the patient move his jaws from opposite directions until the projection provides a centering mark on the other plate; removing at least the other plate from the oral cavity; forming a recess in the place of the centering mark; repositioning the other plate in the oral cavity; having the patient move his jaws until the projection partially enters the recess; and connecting the plates to each other to form a compact aligning assembly prior to the removal thereof from the oral cavity.

2. A method of determining correct mandibular position particularly in prosthodontic and orthodontic work, comprising the steps of providing two prefabricated, substantially flat, rigid plates of a standard shape and made of plastic material, one of said plates having a bore therein, and an externally threaded pin fixed in the bore, the free end of said pin being of ball-shaped configuration; marking the edges of said plates according to the inner contour of existent teeth; adjusting the edges of the plates by cutting off the portions thereof exceeding the marked contours; positioning the adjusted plates in the oral cavity to rest on the upper gum and the lower gum, respectively whereby the ball-shaped end of the pin abuts the other plate; having the patient move his jaws from opposite directions until the ball-shaped end provides a centering mark on the other plate; removing at least the other plate from the oral cavity; forming a bore having a diameter slightly smaller than the diameter of the ball-shaped end in a place determined by the centering mark; repositioning the other plate in the oral cavity; having the patient move his jaws until the ball-shaped end partially enters the bore; and connecting the plates to each other by synthetic plastic material to form a compact aligning assembly prior to the removal thereof from the oral cavity.

* * * * *